(12) United States Patent
Hahn et al.

(10) Patent No.: US 8,207,128 B2
(45) Date of Patent: Jun. 26, 2012

(54) POLYPEPTIDE INHIBITING TRANSMIGRATION OF LEUKOCYTES OR GROWTH AND/OR METASTASIS OF CANCER CELLS, AND FUSION PROTEIN THEREOF

(75) Inventors: Jang-Hee Hahn, Chuncheon-si (KR); Kyoung-Jin Lee, Seoul (KR); Dong-Min Kang, Chuncheon-si (KR)

(73) Assignee: Supadelixir Inc., Kangwon-do (KR)

(*) Notice: Subject to any disclaimer, the term of this patent is extended or adjusted under 35 U.S.C. 154(b) by 456 days.

(21) Appl. No.: 11/991,310

(22) PCT Filed: Sep. 20, 2006

(86) PCT No.: PCT/KR2006/003728
§ 371 (c)(1),
(2), (4) Date: Feb. 29, 2008

(87) PCT Pub. No.: WO2007/037601
PCT Pub. Date: Apr. 5, 2007

(65) Prior Publication Data
US 2010/0286064 A1    Nov. 11, 2010

(30) Foreign Application Priority Data

Sep. 28, 2005 (KR) .................. 10-2005-0090668
Jun. 30, 2006 (KR) .................. 10-2006-0060890
Jul. 19, 2006 (KR) .................. 10-2006-0067440

(51) Int. Cl.
| | |
|---|---|
| A61K 38/17 | (2006.01) |
| A61K 38/07 | (2006.01) |
| A61K 38/08 | (2006.01) |
| A61K 38/10 | (2006.01) |
| C07K 7/06 | (2006.01) |
| C07K 7/08 | (2006.01) |
| C07K 5/10 | (2006.01) |
| C07K 14/435 | (2006.01) |

(52) U.S. Cl. ............ 514/19.8; 514/21.2; 514/21.3; 514/21.4; 514/21.5; 514/21.6; 514/21.7; 514/21.8; 514/21.9; 530/324; 530/325; 530/326; 530/327; 530/329; 530/330

(58) Field of Classification Search .................. None
See application file for complete search history.

(56) References Cited

U.S. PATENT DOCUMENTS 6,277,375 B1 * 8/2001 Ward .................. 424/133.1
2003/0211099 A1   11/2003 Muller et al.

FOREIGN PATENT DOCUMENTS

| WO | WO 01/55312    * | 8/2001 |
| WO | WO 01/68131 A1 | 9/2001 |
| WO | WO 03/020749 A2 * | 3/2003 |

OTHER PUBLICATIONS

Introduction to Cancer from Merck Manual, p. 1. Accessed Mar. 5, 2008.*
Clinical Aspects of Cancer from Merck Manual, pp. 1-4. Accessed Mar. 5, 2008.*
Rheumatoid Arthritis from Merck Manual, pp. 1-12. Accessed Sep. 16, 2009.*
Auerbach R, Akhtar N, Lewis RL, Shinners B, "Angiogenesis assays: Problems and pitfalls," Cancer and Metastasis Reviews, 2000, 19: 167-172.*
Gura Trisha, "SYstems for identifying new drugs are often faulty," Science, 1997, 278: 1041-1042.*
Jain RK, "Barriers to drug discovery in solid tumors," Scientific American, 1994, 58-65.*
Dementia from Merck Manual, pp. 1-17. Accessed Jul. 29, 2009.*
Mattson MP, "Pathways towards and away from Alzheimer's disease," Nature, 2004, 430: 631-639.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Zetter, B.R., "Adhesion molecules in tumor metastasis", *Cancer Biology*, vol. 4, pp. 219-229, (1993).
Bailly, M., et al., "Regulation of Protrusion shape and Adhesion to the Substratum during Chemotactic Responses of Mammalian Carcinoma Cells", *Experimental Cell Research*, vol. 241, pp. 285-299 (1998).
Frisch, S.M., et al., "Control of Adhesion-Dependent Cell Survival by Focal Adhesion Kinase", *Journal of Cell Biology*, vol. 134, pp. 793-799, (Aug. 1996).

(Continued)

*Primary Examiner* — Julie Ha
(74) *Attorney, Agent, or Firm* — Nath, Glodberg & Meyer; Mihsuhn Koh

(57) ABSTRACT

Described is a polypeptide inhibiting the transmigration of leukocytes or the growth and/or metastasis of cancer cells, a fusion protein thereof, a polynucleotide encoding the polypeptide, a vector including the polynucleotide, and a transformant transformed with the vector. Described is also a pharmaceutical composition for the prevention or treatment of inflammatory diseases, or the inhibition of the growth and/or metastasis of cancer cells including the polypeptide or a fusion protein thereof.

13 Claims, 7 Drawing Sheets

OTHER PUBLICATIONS

Hannigan, G.E., et al, "Regulation of cell adhesion and anchorage-dependent growth by a new $\beta_1$-integrin-linked protein kinase", *Nature*, vol. 379, pp. 91-96, (Jan. 4, 1996).

Hahn, J-H, et al., "CD99 (MIC2) Regulates the LFA-A/ICAM-1-Mediated Adhesion of Lymphocytes, and Its Gene Encodes Both Positive and Negative Regulators of Cellular Adhesion", *Journal of Immunology*, vol. vol. 159, pp. 2250-2258, (1997).

Banting, G.S., et al., "The *MIC2* Gene Product: Epitope Mapping and Structural Prediction Analysis Define an Intergral Membrane Protein", *Molecular Immunology*, vol. 26, No. 2, pp. 181-188, (1989).

Bernard, A., et al., "A T Cell Surface Molecule Different From CD2 Is Involved in Spontaneous Rosette Formation With Erythrocytes", *Journal of Immunology*, vol. 140, No. 6, pp. 1802-1807, (Mar. 15, 1988).

Kim, Y-K, "Regulation of MMP-9 gene expression by CD99 type II in the monocytes", thesis submission, Kangwon National University, pp. 39-40, (Feb. 2004).

Suh, JS, "Control of Invasiveness of Human Breast Carcinoma Cell Line MCF-7 by CD99 Molecule", thesis submission, Kangwon National University, pp. 35-36, (Feb. 2002).

Schenkel, A.R., et al., "CD99 plays a major role in the migration of monocytes through endothelial junctions", *Nature Immunology*, vol. 3 No. 2, pp. 143-150, (Feb. 2002).

Lee, S-I, et al., "Suppression of the Onset and Progression of Collagen-Induced Arthritis by Chebulagic Acid Screened From a Natural Product Library", *Arthritis & Rheumatism*, vol. 52, No. 1, pp. 345-353, (Jan. 2005).

Scotland, K., et al., "CD99 Engagement: An Effective Therapeutic Strategy for Ewing Tumors", *Cancer Research*, vol. 69, pp. 5134-5142, (Sep. 15, 2000).

* cited by examiner

[Fig. 1]
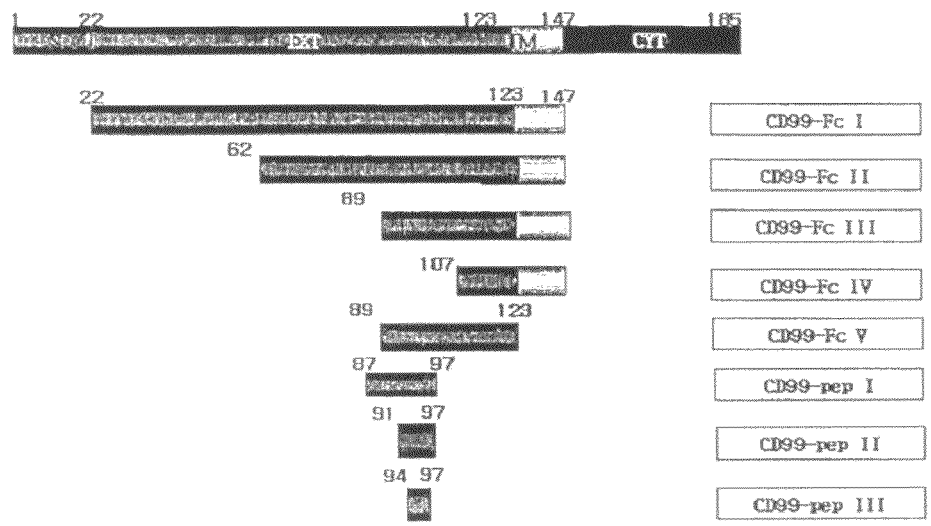
[Fig. 2]
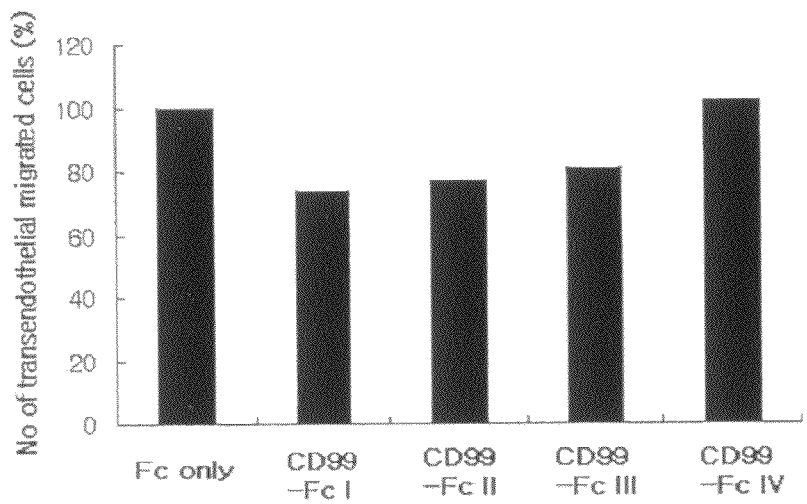
[Fig. 3]
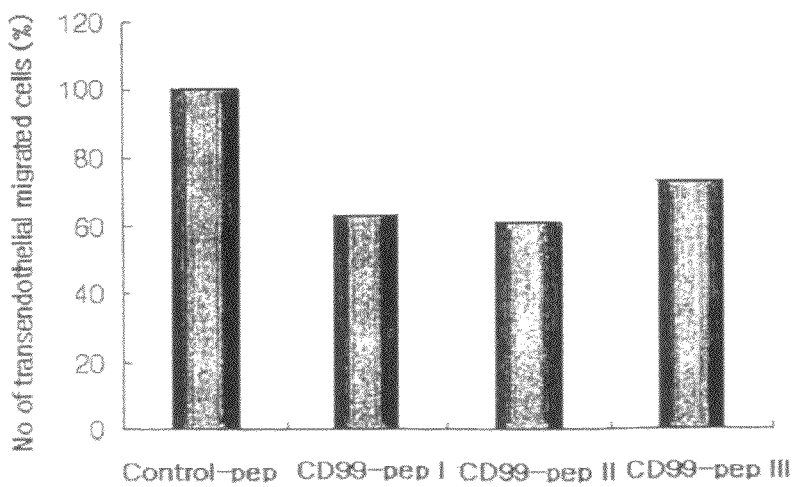

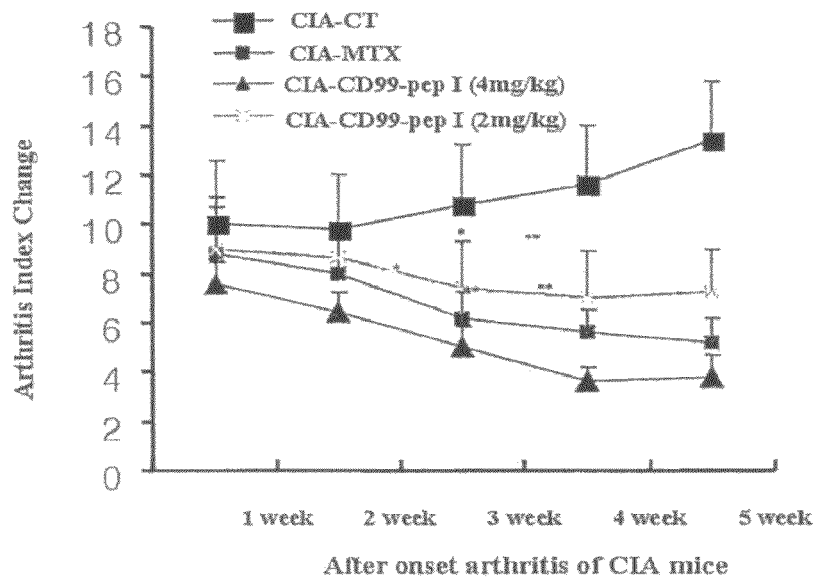
[Fig. 4]
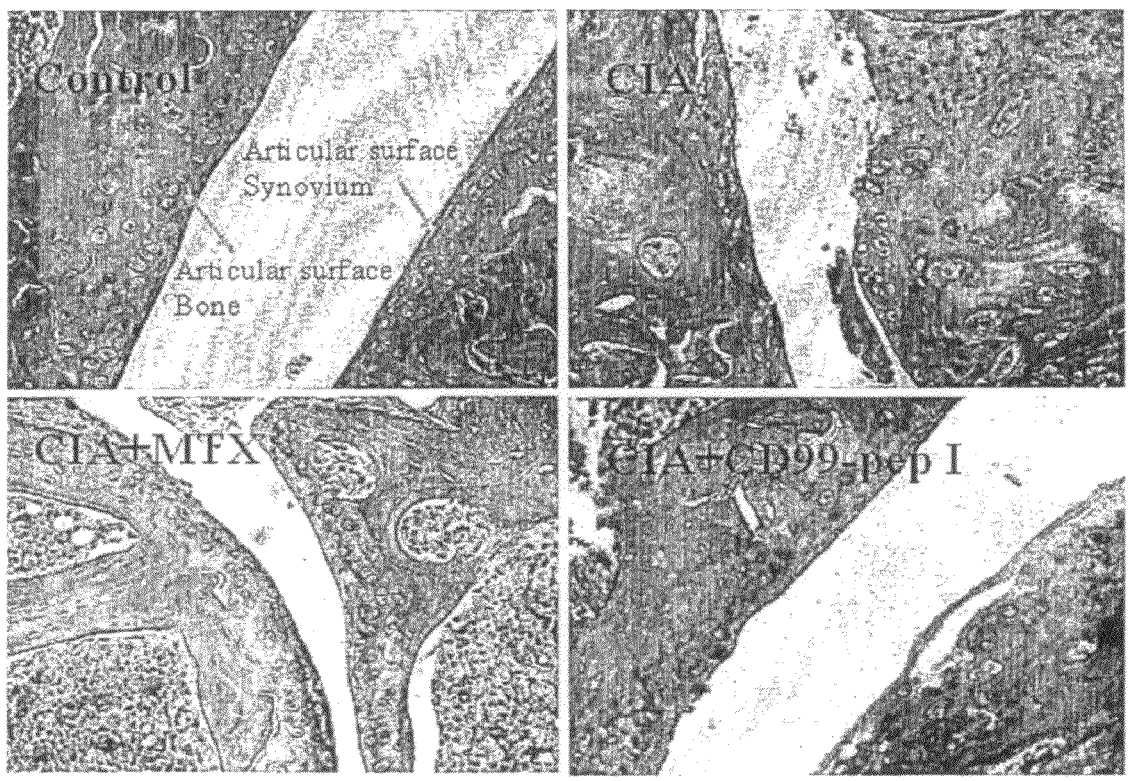
[Fig. 5]

[Fig. 6]
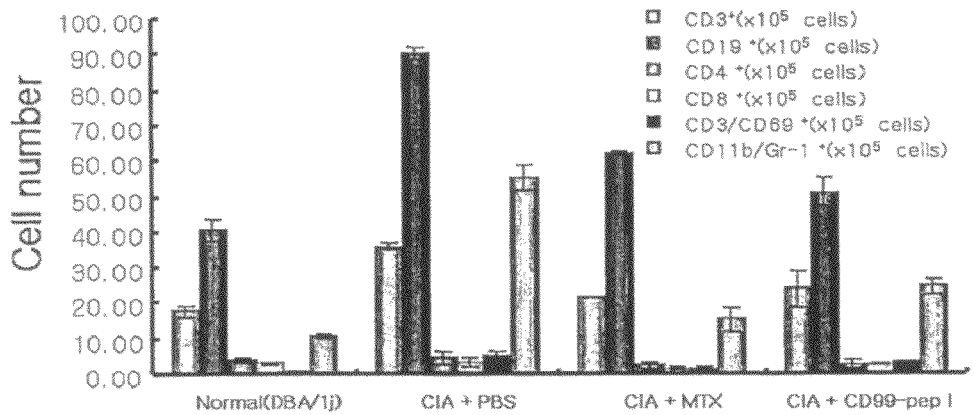
[Fig. 7]
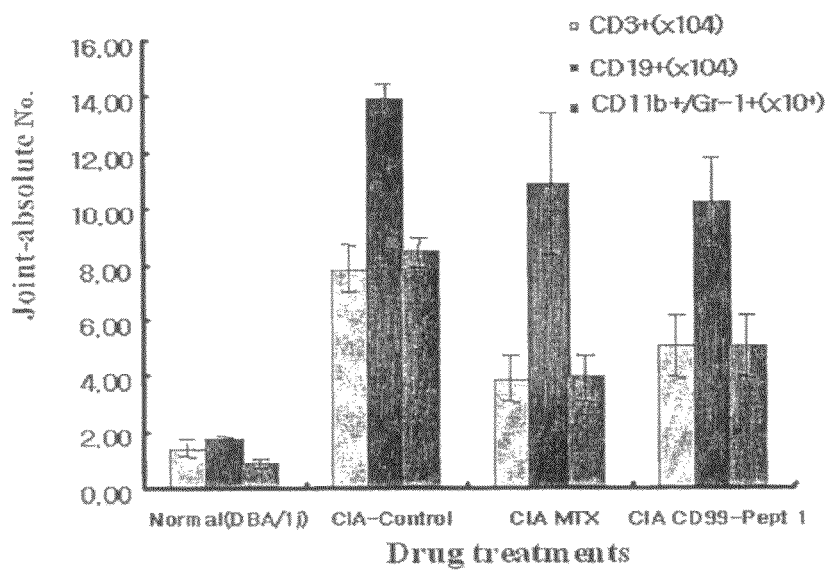
[Fig. 8]
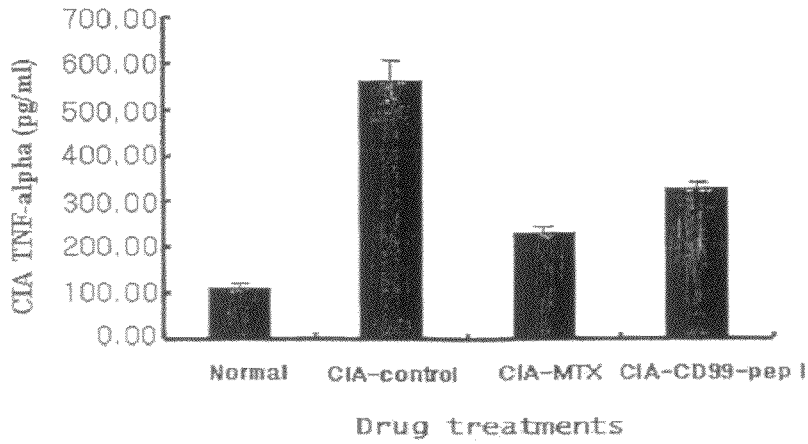

[Fig. 9]
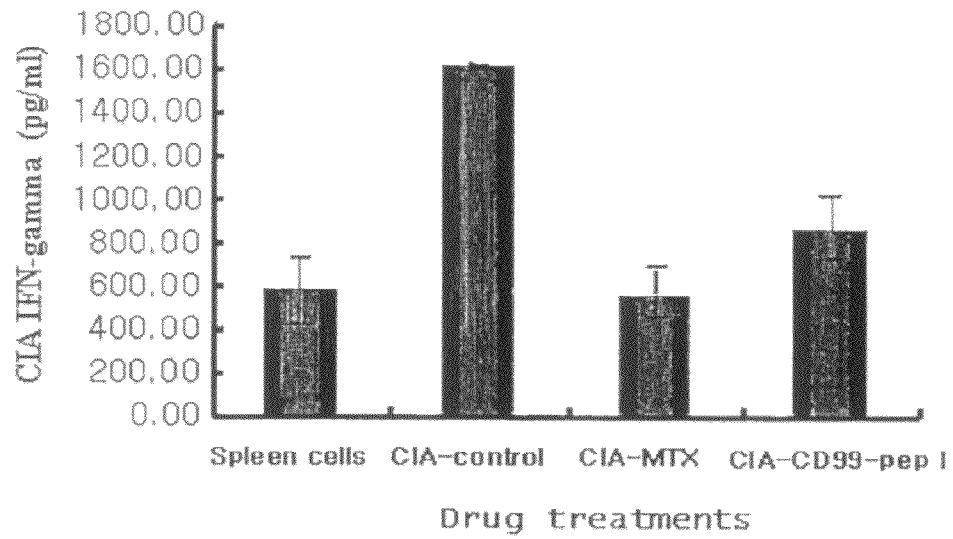
[Fig. 10]
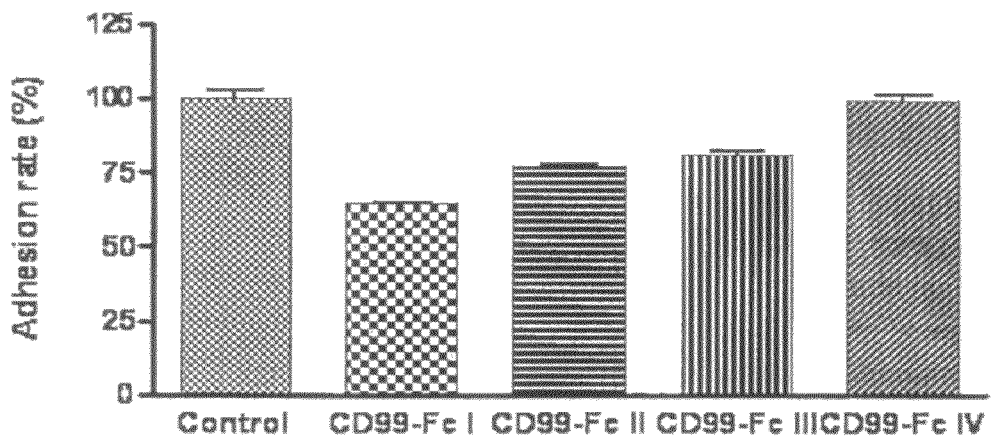
[Fig. 11]
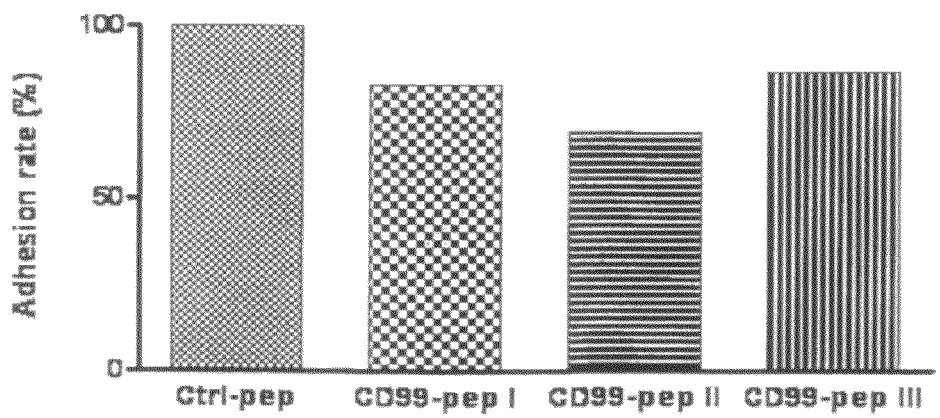

[Fig. 12]
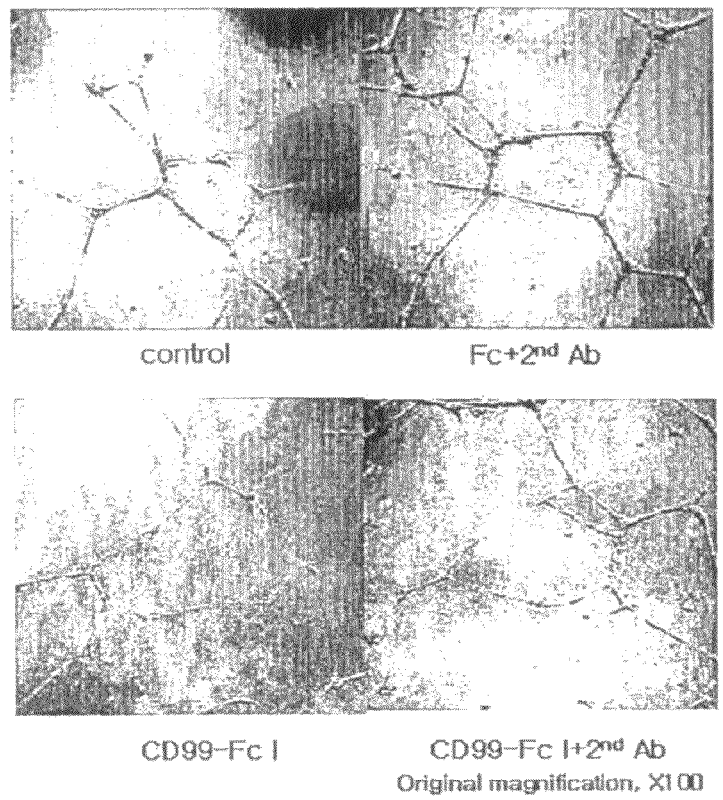
control      Fc+2nd Ab
CD99-Fc I      CD99-Fc I+2nd Ab
Original magnification, X100
[Fig. 13]
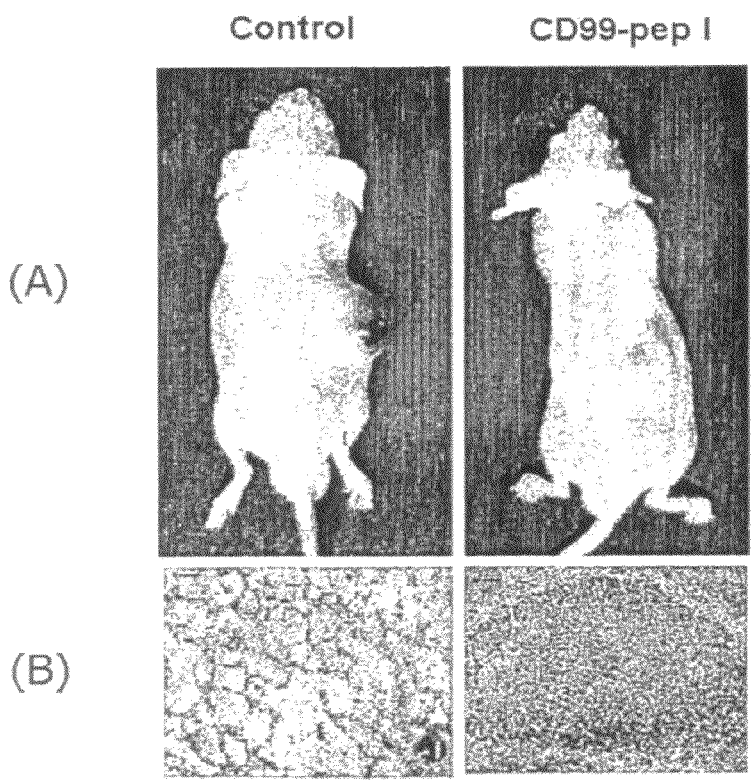
Control      CD99-pep I
(A)
(B)

[Fig. 14]
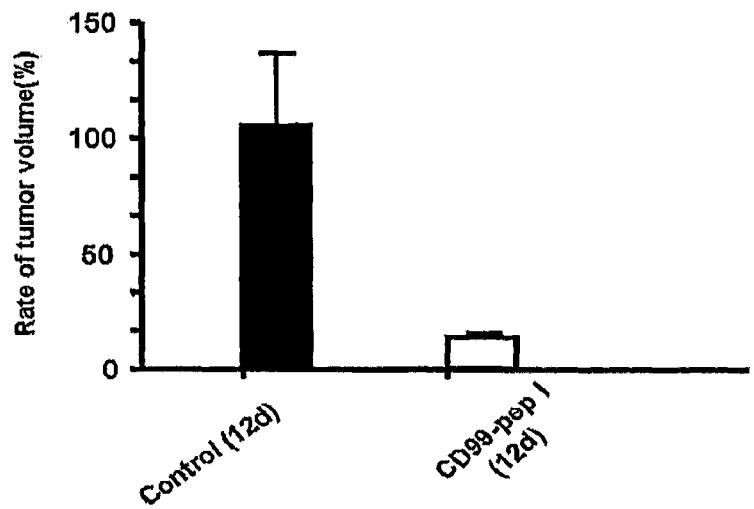
[Fig. 15]
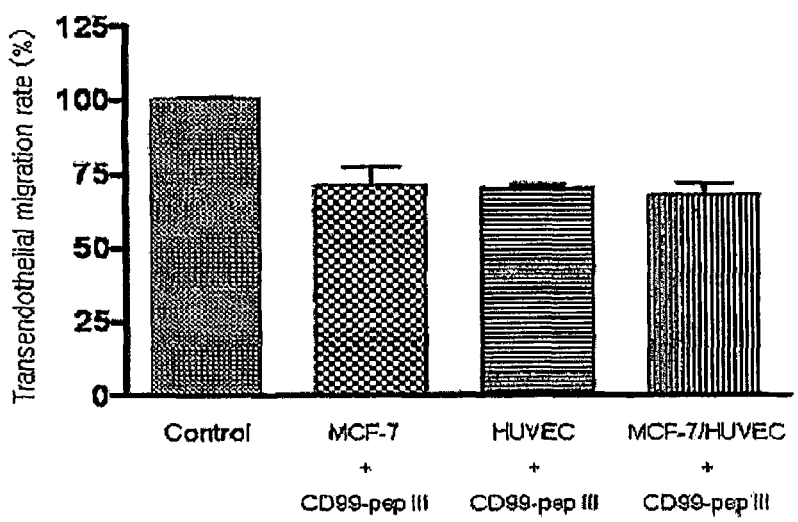
[Fig. 16]
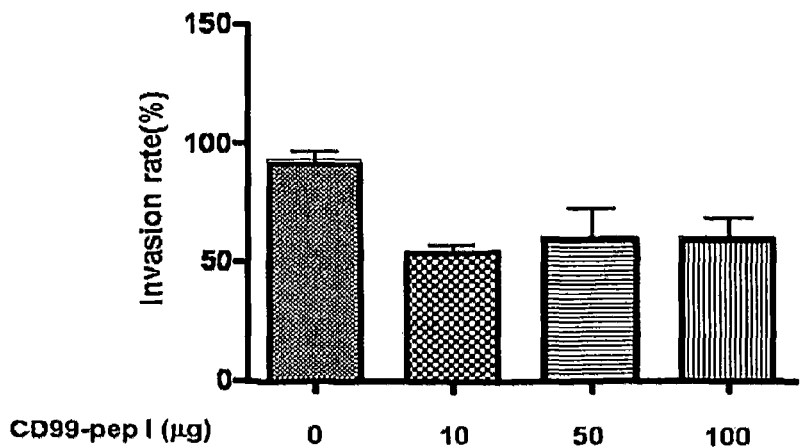

[Fig. 17]
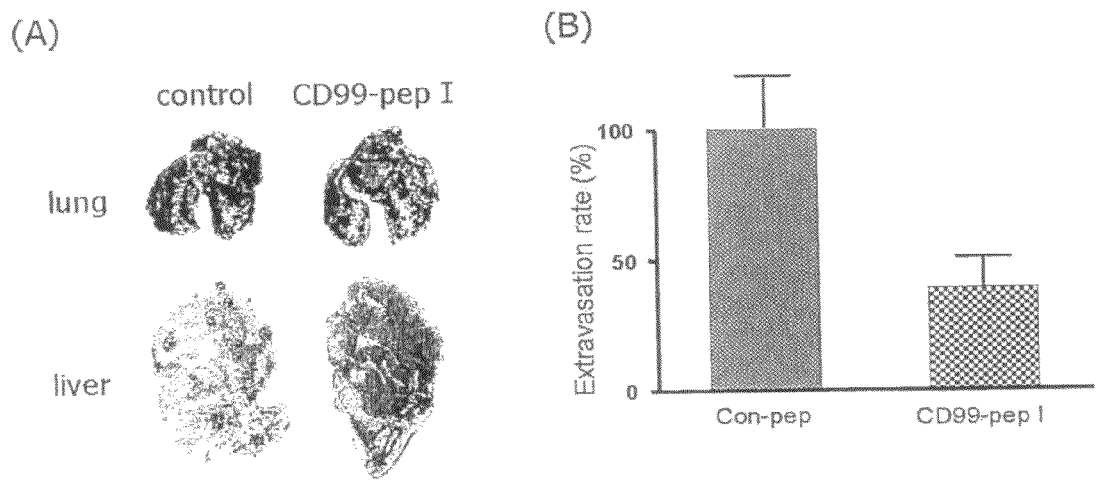

SEQUENCE LISTING

```
<160> NUMBER OF SEQ ID NOS: 27

<210> SEQ ID NO 1
<211> LENGTH: 185
<212> TYPE: PRT
<213> ORGANISM: Homo sapiens
<220> FEATURE:
<221> NAME/KEY: misc_feature
<222> LOCATION: (1)..(185)
<223> OTHER INFORMATION: Xaa all represent any naturally-occuring
      amino acid

<400> SEQUENCE: 1

Met Ala Arg Gly Ala Ala Leu Ala Leu Leu Leu Phe Gly Leu Leu Gly
  1               5                  10                  15

Val Leu Val Ala Ala Pro Asp Gly Gly Phe Asp Leu Ser Asp Ala Leu
                 20                  25                  30

Pro Asp Asn Glu Asn Lys Lys Pro Thr Ala Ile Pro Lys Lys Pro Ser
             35                  40                  45

Ala Gly Asp Asp Phe Asp Leu Gly Asp Ala Val Val Asp Gly Glu Asn
         50                  55                  60

Asp Asp Pro Arg Pro Pro Asn Pro Pro Lys Pro Met Pro Asn Pro Asn
 65                  70                  75                  80

Pro Asn His Pro Ser Ser Ser Gly Xaa Xaa Ser Asp Xaa Asp Leu Xaa
                 85                  90                  95

Asp Xaa Val Ser Gly Gly Glu Gly Lys Gly Gly Ser Asp Gly Gly Gly
                100                 105                 110

Ser His Arg Lys Glu Gly Glu Glu Ala Asp Ala Pro Gly Val Ile Pro
            115                 120                 125

Gly Ile Val Gly Ala Val Val Val Ala Val Ala Gly Ala Ile Ser Ser
        130                 135                 140

Phe Ile Ala Tyr Gln Lys Lys Lys Leu Cys Phe Lys Glu Asn Ala Glu
145                 150                 155                 160

Gln Gly Glu Val Asp Met Glu Ser His Arg Asn Ala Asn Ala Glu Pro
                165                 170                 175

Ala Val Gln Arg Thr Leu Leu Glu Lys
            180                 185

<210> SEQ ID NO 2
<211> LENGTH: 126
<212> TYPE: PRT
<213> ORGANISM: Homo sapiens
<220> FEATURE:
```

<221> NAME/KEY: misc_feature
<222> LOCATION: (1)..(126)
<223> OTHER INFORMATION: Xaa all represent any naturally-occuring
      amino acid

<400> SEQUENCE: 2

Pro Asp Gly Gly Phe Asp Leu Ser Asp Ala Leu Pro Asp Asn Glu Asn
1               5                   10                  15

Lys Lys Pro Thr Ala Ile Pro Lys Lys Pro Ser Ala Gly Asp Asp Phe
            20                  25                  30

Asp Leu Gly Asp Ala Val Val Asp Gly Glu Asn Asp Asp Pro Arg Pro
        35                  40                  45

Pro Asn Pro Pro Lys Pro Met Pro Asn Pro Asn Pro Asn His Pro Ser
    50                  55                  60

Ser Ser Gly Xaa Xaa Ser Asp Xaa Asp Leu Xaa Asp Xaa Val Ser Gly
65                  70                  75                  80

Gly Glu Gly Lys Gly Gly Ser Asp Gly Gly Ser His Arg Lys Glu
                85                  90                  95

Gly Glu Glu Ala Asp Ala Pro Gly Val Ile Pro Gly Ile Val Gly Ala
                100                 105                 110

Val Val Val Ala Val Ala Gly Ala Ile Ser Ser Phe Ile Ala
            115                 120                 125

<210> SEQ ID NO 3
<211> LENGTH: 86
<212> TYPE: PRT
<213> ORGANISM: Homo sapiens
<220> FEATURE:
<221> NAME/KEY: misc_feature
<222> LOCATION: (1)..(86)
<223> OTHER INFORMATION: Xaa all represent any naturally-occuring
      amino acid

<400> SEQUENCE: 3

Gly Glu Asn Asp Asp Pro Arg Pro Pro Asn Pro Pro Lys Pro Met Pro
1               5                   10                  15

Asn Pro Asn Pro Asn His Pro Ser Ser Ser Gly Xaa Xaa Ser Asp Xaa
            20                  25                  30

Asp Leu Xaa Asp Xaa Val Ser Gly Gly Glu Gly Lys Gly Gly Ser Asp
        35                  40                  45

Gly Gly Gly Ser His Arg Lys Glu Gly Glu Glu Ala Asp Ala Pro Gly
    50                  55                  60

Val Ile Pro Gly Ile Val Gly Ala Val Val Val Ala Val Ala Gly Ala
65                  70                  75                  80

Ile Ser Ser Phe Ile Ala
                85

<210> SEQ ID NO 4
<211> LENGTH: 59
<212> TYPE: PRT
<213> ORGANISM: Homo sapiens
<220> FEATURE:
<221> NAME/KEY: misc_feature
<222> LOCATION: (1)..(59)
<223> OTHER INFORMATION: Xaa all represent any naturally-occuring
      amino acid

<400> SEQUENCE: 4

Xaa Xaa Ser Asp Xaa Asp Leu Xaa Asp Xaa Val Ser Gly Gly Glu Gly
1               5                   10                  15

Lys Gly Gly Ser Asp Gly Gly Gly Ser His Arg Lys Glu Gly Glu Glu
            20                  25                  30

```
Ala Asp Ala Pro Gly Val Ile Pro Gly Ile Val Gly Ala Val Val Val
        35                  40                  45

Ala Val Ala Gly Ala Ile Ser Ser Phe Ile Ala
    50                  55

<210> SEQ ID NO 5
<211> LENGTH: 35
<212> TYPE: PRT
<213> ORGANISM: Homo sapiens
<220> FEATURE:
<221> NAME/KEY: misc_feature
<222> LOCATION: (1)..(35)
<223> OTHER INFORMATION: Xaa all represent any naturally-occuring
      amino acid

<400> SEQUENCE: 5

Xaa Xaa Ser Asp Xaa Asp Leu Xaa Asp Xaa Val Ser Gly Gly Glu Gly
1               5                   10                  15

Lys Gly Gly Ser Asp Gly Gly Ser His Arg Lys Glu Gly Glu Glu
            20                  25                  30

Ala Asp Ala
        35

<210> SEQ ID NO 6
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: Xaa all represent any naturally-occuring
      amino acid

<400> SEQUENCE: 6

Ser Gly Xaa Xaa Ser Asp Xaa Asp Leu Xaa Asp
1               5                   10

<210> SEQ ID NO 7
<211> LENGTH: 7
<212> TYPE: PRT
<213> ORGANISM: Homo sapiens
<220> FEATURE:
<221> NAME/KEY: misc_feature
<222> LOCATION: (1)..(7)
<223> OTHER INFORMATION: Xaa all represent any naturally-occuring
      amino acid

<400> SEQUENCE: 7

Ser Asp Xaa Asp Leu Xaa Asp
1               5

<210> SEQ ID NO 8
<211> LENGTH: 4
<212> TYPE: PRT
<213> ORGANISM: Homo sapiens
<220> FEATURE:
<221> NAME/KEY: misc_feature
<222> LOCATION: (1)..(4)
<223> OTHER INFORMATION: Xaa all represent any naturally-occuring
      amino acid

<400> SEQUENCE: 8

Asp Leu Xaa Asp
1

<210> SEQ ID NO 9
<211> LENGTH: 126
```

<212> TYPE: PRT
<213> ORGANISM: Homo sapiens

<400> SEQUENCE: 9

```
Pro Asp Gly Gly Phe Asp Leu Ser Asp Ala Leu Pro Asp Asn Glu Asn
 1               5                  10                  15

Lys Lys Pro Thr Ala Ile Pro Lys Lys Pro Ser Ala Gly Asp Asp Phe
             20                  25                  30

Asp Leu Gly Asp Ala Val Val Asp Gly Glu Asn Asp Asp Pro Arg Pro
         35                  40                  45

Pro Asn Pro Pro Lys Pro Met Pro Asn Pro Asn Pro Asn His Pro Ser
     50                  55                  60

Ser Ser Gly Ser Phe Ser Asp Ala Asp Leu Ala Asp Gly Val Ser Gly
 65                  70                  75                  80

Gly Glu Gly Lys Gly Gly Ser Asp Gly Gly Ser His Arg Lys Glu
             85                  90                  95

Gly Glu Glu Ala Asp Ala Pro Gly Val Ile Pro Gly Ile Val Gly Ala
            100                 105                 110

Val Val Val Ala Val Ala Gly Ala Ile Ser Ser Phe Ile Ala
            115                 120                 125
```

<210> SEQ ID NO 10
<211> LENGTH: 86
<212> TYPE: PRT
<213> ORGANISM: Homo sapiens

<400> SEQUENCE: 10

```
Gly Glu Asn Asp Asp Pro Arg Pro Pro Asn Pro Pro Lys Pro Met Pro
 1               5                  10                  15

Asn Pro Asn Pro Asn His Pro Ser Ser Ser Gly Ser Phe Ser Asp Ala
             20                  25                  30

Asp Leu Ala Asp Gly Val Ser Gly Gly Glu Gly Lys Gly Gly Ser Asp
         35                  40                  45

Gly Gly Gly Ser His Arg Lys Glu Gly Glu Glu Ala Asp Ala Pro Gly
     50                  55                  60

Val Ile Pro Gly Ile Val Gly Ala Val Val Val Ala Val Ala Gly Ala
 65                  70                  75                  80

Ile Ser Ser Phe Ile Ala
             85
```

<210> SEQ ID NO 11
<211> LENGTH: 59
<212> TYPE: PRT
<213> ORGANISM: Homo sapiens

<400> SEQUENCE: 11

```
Ser Phe Ser Asp Ala Asp Leu Ala Asp Gly Val Ser Gly Gly Glu Gly
 1               5                  10                  15

Lys Gly Gly Ser Asp Gly Gly Ser His Arg Lys Glu Gly Glu Glu
             20                  25                  30

Ala Asp Ala Pro Gly Val Ile Pro Gly Ile Val Gly Ala Val Val Val
         35                  40                  45

Ala Val Ala Gly Ala Ile Ser Ser Phe Ile Ala
     50                  55
```

<210> SEQ ID NO 12
<211> LENGTH: 41
<212> TYPE: PRT
<213> ORGANISM: Homo sapiens

```
<400> SEQUENCE: 12

Gly Ser Asp Gly Gly Ser His Arg Lys Glu Gly Glu Glu Ala Asp
 1               5                  10                  15

Ala Pro Gly Val Ile Pro Gly Ile Val Gly Ala Val Val Ala Val
                20                  25                  30

Ala Gly Ala Ile Ser Ser Phe Ile Ala
                35                  40

<210> SEQ ID NO 13
<211> LENGTH: 35
<212> TYPE: PRT
<213> ORGANISM: Homo sapiens

<400> SEQUENCE: 13

Ser Phe Ser Asp Ala Asp Leu Ala Asp Gly Val Gly Gly Glu Gly
 1               5                  10                  15

Lys Gly Gly Ser Asp Gly Gly Ser His Arg Lys Glu Gly Glu Glu
                20                  25                  30

Ala Asp Ala
            35

<210> SEQ ID NO 14
<211> LENGTH: 11
<212> TYPE: PRT
<213> ORGANISM: Homo sapiens

<400> SEQUENCE: 14

Ser Gly Ser Phe Ser Asp Ala Asp Leu Ala Asp
 1               5                  10

<210> SEQ ID NO 15
<211> LENGTH: 7
<212> TYPE: PRT
<213> ORGANISM: Homo sapiens

<400> SEQUENCE: 15

Ser Asp Ala Asp Leu Ala Asp
 1               5

<210> SEQ ID NO 16
<211> LENGTH: 4
<212> TYPE: PRT
<213> ORGANISM: Homo sapiens

<400> SEQUENCE: 16

Asp Leu Ala Asp
 1

<210> SEQ ID NO 17
<211> LENGTH: 6
<212> TYPE: PRT
<213> ORGANISM: Homo sapiens
<220> FEATURE:
<223> OTHER INFORMATION: poly-His Fragment

<400> SEQUENCE: 17

His His His His His His
 1               5

<210> SEQ ID NO 18
<211> LENGTH: 378
<212> TYPE: DNA
<213> ORGANISM: Homo sapiens
```

<400> SEQUENCE: 18

```
ccggatggtg gtttcgattt atccgatgcc cttcctgaca atgaaaacaa gaaacccact      60
gcaatcccca agaaacccag tgctggggat gactttgact taggagatgc tgttgttgat     120
ggagaaaatg acgacccacg accaccgaac ccacccaaac cgatgccaaa tccaaacccc     180
aaccacccta gttcctccgg tagcttttca gatgctgacc ttgcggatgg cgtttcaggt     240
ggagaaggaa aaggaggcag tgatggtgga ggcagccaca ggaaagaagg ggaagaggcc     300
gacgccccag gcgtgatccc cgggattgtg ggggctgtcg tggtcgccgt ggctggagcc     360
atctctagct tcattgct                                                    378
```

<210> SEQ ID NO 19
<211> LENGTH: 258
<212> TYPE: DNA
<213> ORGANISM: Homo sapiens

<400> SEQUENCE: 19

```
ggagaaaatg acgacccacg accaccgaac ccacccaaac cgatgccaaa tccaaacccc      60
aaccacccta gttcctccgg tagcttttca gatgctgacc ttgcggatgg cgtttcaggt     120
ggagaaggaa aaggaggcag tgatggtgga ggcagccaca ggaaagaagg ggaagaggcc     180
gacgccccag gcgtgatccc cgggattgtg ggggctgtcg tggtcgccgt ggctggagcc     240
atctctagct tcattgct                                                    258
```

<210> SEQ ID NO 20
<211> LENGTH: 177
<212> TYPE: DNA
<213> ORGANISM: Homo sapiens

<400> SEQUENCE: 20

```
agcttttcag atgctgacct tgcggatggc gtttcaggtg agaaggaaa aggaggcagt       60
gatggtggag gcagccacag gaaagaaggg gaagaggccg acgccccagg cgtgatcccc     120
gggattgtgg gggctgtcgt ggtcgccgtg gctggagcca tctctagctt cattgct        177
```

<210> SEQ ID NO 21
<211> LENGTH: 123
<212> TYPE: DNA
<213> ORGANISM: Homo sapiens

<400> SEQUENCE: 21

```
ggcagtgatg gtggaggcag ccacaggaaa gaaggggaag aggccgacgc cccaggcgtg      60
atccccggga ttgtgggggc tgtcgtggtc gccgtggctg gagccatctc tagcttcatt     120
gct                                                                    123
```

<210> SEQ ID NO 22
<211> LENGTH: 105
<212> TYPE: DNA
<213> ORGANISM: Homo sapiens

<400> SEQUENCE: 22

```
agcttttcag atgctgacct tgcggatggc gtttcaggtg agaaggaaa aggaggcagt       60
gatggtggag gcagccacag gaaagaaggg gaagaggccg acgcc                     105
```

<210> SEQ ID NO 23
<211> LENGTH: 33
<212> TYPE: DNA
<213> ORGANISM: Homo sapiens

```
<400> SEQUENCE: 23
tccggtagct tttcagatgc tgaccttgcg gat                                33

<210> SEQ ID NO 24
<211> LENGTH: 21
<212> TYPE: DNA
<213> ORGANISM: Homo sapiens

<400> SEQUENCE: 24
tcagatgctg accttgcgga t                                             21

<210> SEQ ID NO 25
<211> LENGTH: 12
<212> TYPE: DNA
<213> ORGANISM: Homo sapiens

<400> SEQUENCE: 25
gaccttgcgg at                                                       12

<210> SEQ ID NO 26
<211> LENGTH: 11
<212> TYPE: PRT
<213> ORGANISM: Mus musculus

<400> SEQUENCE: 26

Ser Gly Gly Ile Ser Asp Ser Asp Leu Ala Asp
  1               5                  10

<210> SEQ ID NO 27
<211> LENGTH: 11
<212> TYPE: PRT
<213> ORGANISM: Homo sapiens

<400> SEQUENCE: 27

Glu Glu Phe Asp Asp Ala Glu Glu Phe Asp Asp
  1               5                  10
```

POLYPEPTIDE INHIBITING TRANSMIGRATION OF LEUKOCYTES OR GROWTH AND/OR METASTASIS OF CANCER CELLS, AND FUSION PROTEIN THEREOF

TECHNICAL FIELD

The present invention relates to a polypeptide inhibiting the transmigration of leukocytes or the growth and/or metastasis of cancer cells, or a fusion protein thereof. The present invention also relates to a polynucleotide encoding the polypeptide, a vector including the polynucleotide, and a transformant transformed with the vector. The present invention also relates to a pharmaceutical composition for the prevention or treatment of inflammatory diseases including the polypeptide or a fusion protein thereof. The present invention also relates to a pharmaceutical composition for inhibiting the growth and/or metastasis of cancer cells including the polypeptide or a fusion protein thereof.

The Sequence Listing submitted in text format (.txt) on Mar. 6, 2012, named "11991310 sequence listing Corrected.txt", (created on Monday, Mar. 5, 2012, 12.3 KB), is incorporated herein by reference.

BACKGROUND ART

An inflammatory response is known as a protective response of living organism for rehabilitating the structures and functions of tissues damaged by infection, trauma, etc. Mobilization of leukocytes to a focus of inflammation is critical for the rapid resolution of infections and restoration of tissue damages resulting from a variety of injuries. However, a misdirected or prolonged inflammatory response causes damage to the body's tissues or diseases. For example, inflammatory diseases are caused by bacterial or viral infection, e.g., cerebrospinal meningitis, enteritis, dermatitis, uveitis, encephalitis, or adult respiratory distress syndrome, or non-infectious factors, e.g., trauma, autoimmune diseases, or organ transplantation rejection. Inflammatory diseases are classified into acute and chronic inflammatory diseases according to symptoms or pathological features. Acute inflammation such as allergy or bacterial/viral infection is manifested as local signs such as a change in bloodstream, blood vessel size, and vascular permeability, and the recruitment of leukocytes. In contrast, a main pathological feature of chronic inflammation such as rheumatoid arthritis, artherosclerosis, chronic kidney infection, or hepatocirrhosis is a continuous emigration of macrophages, lymphocytes, or plasma cells into foci of inflammation due to recurrence of inflammatory factors, thereby causing a long-lasting inflammatory response.

In order to induce an inflammatory response, the emigration of leukocytes into inflammation foci is an essential event. Many cell adhesion molecules are implicated in the emigration of leukocytes. That is, the emigration of leukocytes includes a rolling stage in which leukocytes are mobilized to the blood vessels of inflamed sites by chemokine secreted from the inflamed sites and then rolled on surfaces of vascular endothelial cells while reducing the velocity of cell movement; an adhesion stage in which the leukocytes stops rolling and are firmly adhered to the vascular endothelial cells; and a transmigration stage wherein the leukocytes migrate through capillary vessels and basement membranes. The final stage, i.e., the transmigration stage is also called "diapedesis" or "transendothelial migration".

Cancer cells induced by carcinogens proliferate rapidly relative to normal cells, thereby forming tumor masses, invading surrounding tissues, and interfering with normal body functions. Cancer cells bring nutrients and oxygen by inducing angiogenesis, and metastasis thereof is also caused by angiogenesis. Although cancer cells grow infinitely at specific sites, they can also leave the sites from which they originated, migrate to and grow in new sites, whose process is called "metastasis". Metastasis involve several key steps: conversion of cancer cells to migratory mesenchymal cells, dissociation of the mesenchymal cells from the original tumor sites, invasion into and spread through surrounding connective tissues and capillary vessels, migration through blood vessels, escape from the blood vessels, migration through connective tissues, and proliferation in secondary sites.

Expression and activation of cell adhesion molecules on surfaces of tumor cells play a very important role in tumor metastasis (Zetter, B. R. (1993). Adhesion molecules in tumor metastasis. Semin Cancer Biol. 4: 219). Tumor metastasis is induced by regulating the expression pattern and activity of cell adhesion molecules on surfaces of tumor cells. In order to understand the metastasis of tumor cells, it is prerequisite to understand cell adhesion molecules and substances for regulating the expression and functions of the cell adhesion molecules (Bailly, M., Yan, L., Whitesides, G. M., Condeelis, J. S., and Segall, J. E. (1998). regulation of Protusion Shape and Adhesion to the sustratum during chemoacic esponses of mammalian carcinoma cells. Exp Cell Res. 241: 285; Frisch, S. M., Vuori, K., Ruoslahti, E., and Chan-Hui., P. (1996). Control of adhesion-dependent cell survival by focal adhesion kinase. J Cell Biol 134: 793; and Hannigan, G. E., Leung-Hagesteijn, C., Fitz-Gibbon, L., Coppolino, M. G., Radeva, G., Filmus, J., Bell, J. C., and Dedhar, S. (1996). Regulation of cell adhesion and anchorage-dependent growth by a new β1-integrin-linked protein kinase. Nature 379: 91).

Meanwhile, the present inventors have disclosed that CD99 (MIC2) molecule, which is one of the transmembrane proteins, regulates an intercellular adhesion by regulating a cell surface expression of LFA-1 (Hahn, J. H., Kim, M. K., Choi, E. Y., Kim, S. H., Sohn, H. W., Ham, D. I., Chung, D. H., Kim, T. J., Lee, W. J., Park, C. K., Ree, H. J., and Park, S. H. (1997) CD99 (MIC2) regulates the LFA-1/ICAM-1-mediated adhesion of lymphocytes, and its gene encodes both positive and negative regulators of cellular adhesion. J. Immunol. 159: 2250). CD99 is a type I transmembrane protein composed of a glycosylated extracellular domain, a transmembrane domain, and a short intracellular domain (Banting, G. S., Pym, B., Darling, S. M., and Goodfellow P. N. (1989). The MIC2 gene product: epitope mapping and structural prediction analysis define an integral membrane protein. Mol. Immunol. 26: 181). Although there has not been much research about the function of the CD99 molecule, it has been presumed that the CD99 molecule is associated with cell adhesion, on the basis of the observations that the engagement of the CD99 molecule with anti-CD99 monoclonal antibody induces homotypic cell aggregation of various lymphoid cell lines as well as double-positive thymocytes (Bernard, A., Aubrit, F., Raynal, B., Pham, D., and Boumsell, L. (1988). A T cell surface molecule different from CD2 is involved in spontaneous rosette formation with erythrocytes. J Immunol 140: 1802; and Bernard, G., Zoccola, D., Deckert, M., Breittmayer, J., Aussel, C., and Bernard. A. (1995). The E2 molecule (CD99) specifically triggers homotypic aggregation of CD4+ CD8+ thymocytes. J. Immunol. 154: 26).

The present inventors have found that CD99 is involved in the migration of monocytes through connective tissues (Kim Y K., 2004. Regulation of MMP-9 gene expression by CD99 type II in the monocytes. Kangwon National University). The present inventors have also disclosed that when CD99 is activated, the function of $\beta_1$ integrin is altered, thereby preventing the adhesion of cancer cells onto extracellular matrices (ECMs). This suggests that CD99 may be involved in metastasis of cancer cells (Suh J S., 2001. Control of invasiveness of human breast carcinoma cell line MCF-7 by CD99 molecule. Kangwon National University). In addition, Muller W A et al. have disclosed that inflammatory diseases can be cured by inhibiting the CD99-mediated transmigration of leukocytes (Schenkel A R, Mamdouh Z, Chen X, Lieman R M, Muller W A (2002) CD99 plays a major role in the migration of monocytes through endothelial junctions. Nat Immunol 3:143; and US. Patent Publication No. 2003/0211099).

DISCLOSURE OF INVENTION

Technical Problem

The present inventors have found that a polypeptide having an amino acid sequence derived from CD99 can prevent the transmigration of leukocytes or the growth and/or metastasis of cancer cells.

Therefore, the present invention provides a polypeptide derived from CD99, inhibiting the transmigration of leukocytes or the growth and/or metastasis of cancer cells, and a fusion protein thereof.

The present invention also provides a polynucleotide encoding the polypeptide and a vector including the polynucleotide.

The present invention also provides a transformant obtained by transforming a host cell with the vector.

The present invention also provides a pharmaceutical composition for the prevention or treatment of inflammatory diseases, including the polypeptide or its fusion protein as an active ingredient and a pharmaceutically acceptable carrier.

The present invention also provides a pharmaceutical composition for inhibiting the growth and/or metastasis of cancer cells, including the polypeptide or its fusion protein as an active ingredient and a pharmaceutically acceptable carrier.

Technical Solution

In accordance with an aspect of the present invention, there is provided a polypeptide consisting of 4-130 amino acids derived from the peptide of SEQ ID NO: 1, said polypeptide comprising an amino acid sequence from position 94 to position 97 of SEQ ID NO: 1; wherein said polypeptide inhibits transmigration of leukocytes or growth and/or metastasis of cancer cells.

In accordance with another aspect of the present invention, there is provided a fusion protein wherein a polyhistidine (poly-His) region is fused to the polypeptide.

In accordance with still another aspect of the present invention, there is provided a polynucleotide encoding the polypeptide.

In accordance with still another aspect of the present invention, there is provided a vector comprising the polynucleotide encoding the polypeptide.

In accordance with still another aspect of the present invention, there is provided a transformant obtained by transforming a host cell with the vector.

In accordance with yet another aspect of the present invention, there is provided a pharmaceutical composition for the prevention or treatment of inflammatory diseases, comprising the polypeptide or its fusion protein as an active ingredient and a pharmaceutically acceptable carrier.

In accordance with a further aspect of the present invention, there is provided a pharmaceutical composition for inhibiting the growth and/or metastasis of cancer cells, comprising the polypeptide or its fusion protein as an active ingredient and a pharmaceutically acceptable carrier.

BRIEF DESCRIPTION OF THE DRAWINGS

FIG. 1 illustrates the structures of polypeptides as set forth in SEQ ID NOs: 2-9;

FIGS. 2 and 3 are graphs illustrating effects of polypeptides of the present invention on the transmigration of a human monocyte cell line, U937;

FIG. 4 is a graph illustrating effects of polypeptides of the present invention on rheumatic inflammation of mice having collagen-induced arthritis;

FIG. 5 shows the degree of corrosion of articular cartilages of a control group and a test group treated with a polypeptide of the present invention;

FIG. 6 is a graph illustrating cell numbers of transmigrated lymphocytes and myeloid cells in the spleens of a control group and a test group treated with a polypeptide of the present invention;

FIG. 7 is a graph illustrating cell numbers of T cells (CD3$^+$), B cells (CD19$^+$), and myeloid cells (CD11b$^+$, Gr-1$^+$) migrated into the joint spaces of a control group and a test group treated with a polypeptide of the present invention;

FIGS. 8 and 9 are graphs illustrating expression levels of TNF-$\alpha$ and IFN-$\gamma$ in the sera of a control group and a test group treated with a polypeptide of the present invention;

FIGS. 10 and 11 are graphs illustrating effects of polypeptides of the present invention on adhesion of HUVEC (Human Umbilical Vein Endothelial Cell) to fibronectin;

FIG. 12 is inverted microscopic images showing effects of polypeptides of the present invention on bFGF-induced tube formation;

FIG. 13 is images showing degree of development of melanoma (A) and degree of angiogenesis (B) in a control group and a test group treated with a polypeptide of the present invention;

FIG. 14 is a graph illustrating melanoma tumor volumes in a control group and a test group treated with a polypeptide of the present invention;

FIG. 15 is a graph illustrating transendothelial migration assays for MCF-7 human breast carcinoma cells after administration of a polypeptide of the present invention;

FIG. 16 is a graph illustrating invasion assay for MCF-7 human breast carcinoma cells after administration of a polypeptide of the present invention;

FIG. 17 is images (A) showing nodules of melanoma cells that have spread to the lungs and liver through transmigration after administration of a polypeptide of the present invention and a graph (B) illustrating the number of the nodules.

MODE FOR THE INVENTION

Throughout the specification, the term "inflammatory diseases" include acute and/or chronic inflammatory diseases, e.g., rheumatoid arthritis, adhesive capsulitis, sinovitis, coxarthritis, osteoarthritis, osteoporosis, periarthritis, multiple sclerosis, osteomyelitis, systemic lupus erythematosus, polymyalgia rheumatica(PMR), Sjogren's Syndrome, progressive systemic sclerosis(scleroderma), ankylosing spondylitis, polymyositis, dermatomyositis, pemphigus, pemphigoid, Type I diabetes mellitus, myasthenia gravis, Hashimoto's thyroditis, Graves' disease, Goodpasture's disease, mixed connective tissue disease, sclerosing cholangitis; inflammatory bowel disease such as Crohn's Disease or ulcerative colitis, inflammatory dermatoses; inflammatory respiratory diseases such as usual interstitial pneumonitis(UIP), lymphoid interstitial pneumonia, giant cell interstitial pneumonia, cellular interstitial pneumonia, desquamative interstitial pneumonia, asbestosis, silicosis, berylliosis, talcosis, pneumoconiosis, Adult Respiratory Distress Syndrome, extrinsic allergic alveolitis; immediate hypersensitivity reactions such as asthma or hayfever; sarcoidosis, Wegener's granulomatosis, various angiitis, chronic active hepatitis, delayed-type hypersensitivity reactions such as poison ivy dermatitis, cutaneous allergies, psoriatic arthritis, Reiter's syndrome, immediate hypersensitivity reactions, rheumatic fever, acute or chronic glomerulonephritis, acute exacerbations, pyelonephritis, cellulitis, cystitis, acute cholecystitis, inflammatory aortic aneurysm, atherosclerosis, Still's disease), Parkinson's disease, Alzheimer's disease. A polypeptide or fusion protein of the present invention can also be administered to patients suffering from diseases involving inflammatory diseases, e.g., reperfusion injuries, autoimmune diseases, organ transplantation rejection or tissue allograft organ rejection, etc. Thus, the "inflammatory diseases" as used herein are meant to comprehend diseases involving inflammatory diseases. A polypeptide or fusion protein of the present invention can be used in rheumatoid arthritis, osteoporosis, respiratory inflammation, autoimmune diseases, and/or organ transplantation rejection, particularly preferably, rheumatoid arthritis, autoimmune diseases, and/or organ transplantation rejection.

The present inventors have made searches for ligand(s) capable of activating a CD99 molecule having an amino acid sequence as set forth in SEQ ID NO: 1. In view that CD99 itself acts as a ligand recognizing a CD99 molecule that is a transmembrane protein, ligands of various lengths were made from CD99 molecule and searches were made using the ligands.

Surprisingly, the present inventors found that polypeptides having certain amino acid sequences derived from CD99 could show anti-inflammatory activity by blocking the transmigration of leukocytes through high-affinity binding to vascular endothelial cells and leukocytes. When the polypeptides were injected into inflamed sites of mice with arthritis, an arthritis index and the transmigration of lymphocytes and granulocytes related thereto were significantly reduced, as compared with control mice. Those results show that the polypeptides have preventive or treatment activity for inflammatory responses.

Furthermore, the present inventors found that polypeptides having the amino acid sequences derived from CD99 could inhibit the growth and/or metastasis of cancer cells by inhibiting angiogenesis through high-affinity binding to surfaces of vascular endothelial cells and inhibiting the migration and transmigration of cancer cells through binding to the cancer cells. When the polypeptides were administered to affected sites of mice with melanoma, tumor growth and metastasis were significantly reduced as compared with control mice. Those results show that the polypeptides have inhibitory activity for the growth and/or metastasis of cancer cells.

The present invention provides a polypeptide consisting of 4-130 amino acids derived from the peptide of SEQ ID NO: 1, said polypeptide comprising an amino acid sequence from position 94 to position 97 of SEQ ID NO: 1; wherein said polypeptide inhibits transmigration of leukocytes or growth and/or metastasis of cancer cells. The polypeptide may be selected from the group consisting of polypeptides as set forth in SEQ ID NOs: 2-8. More preferably, the polypeptide may be selected from the group consisting of polypeptides as set forth in SEQ ID NOs: 9-11 and 13-16.

The present invention also provides a fusion protein wherein a polyhistidine (poly-His) region is fused to the polypeptide. The poly-His region, which is a tag polypeptide, can be used for the separation and purification of the polypeptide of the present invention by binding to a histidine binding resin. In the fusion protein of the present invention, the poly-His region may have an amino acid sequence as set forth in SEQ ID NO: 17.

The present invention also provides a polynucleotide encoding the polypeptide. The polynucleotide can be prepared using a known method in the art. The polynucleotide may have a nucleotide sequence selected from the group consisting of nucleotide sequences as set forth in SEQ ID NOs: 18-20 and 22-25.

The present invention also provides a vector comprising the polynucleotide encoding the polypeptide. Various known cloning vectors, e.g., pPICZαA, B, or C (Invitrogen, U.S.A.), may be used as a cloning vector. Preferably, a vector including DNA encoding a poly-His region, e.g., a pET28a(+) vector (Novagen, U.S.A.) may be used as a cloning vector. The vector of the present invention can be constructed by inserting the polynucleotide encoding the polypeptide into a cloning vector with an appropriate restriction enzyme site using a method commonly known in the art. The vector of the present invention may be directly used in a gene therapeutic composition for the purpose of gene therapy or may be used in the production of transformants.

The present invention also provides a transformant obtained by transforming a host cell with the vector. The host cell is not particularly limited as long as the polypeptide can be effectively expressed. Preferably, the host cell may be selected from microorganisms belonging to the genus *Escherichia* (e.g., *Escherichia coli*), the genus *Pichia* (e.g., X-33 *Pichia*; Invitrogen, U.S.A.), etc.

The present invention also provides a pharmaceutical composition for the prevention or treatment of inflammatory diseases, comprising the polypeptide or its fusion protein as an active ingredient and a pharmaceutically acceptable carrier.

The present invention also provides a pharmaceutical composition for inhibiting the growth and/or metastasis of cancer cells, comprising the polypeptide or its fusion protein as an active ingredient and a pharmaceutically acceptable carrier.

The pharmaceutical compositions of the present invention may include excipients such as lactose or corn starch, lubricants such as magnesium stearate, currently available emulsifiers, suspending agents, buffers, isotonic agents, etc. The pharmaceutical compositions of the present invention can be administered orally or parenterally. Preferably, the pharmaceutical compositions of the present invention can be formulated into parenteral dosage forms. For intramuscular, intraperitoneal, subcutaneous, or intravenous administration, a sterilized solution of an active ingredient is generally prepared. In this case, the sterilized solution may include a buffer to achieve a desired pH value. With respect to formulations for intravenous administration, an isotonic agent may be used to render the formulations isotonic. The pharmaceutical compositions of the present invention can be formulated into aqueous solutions including a pharmaceutically acceptable carrier such as a saline of pH 7.4. The aqueous solutions can be introduced into a patient's intramuscular blood stream by local bolus injection.

The pharmaceutical composition of the present invention can be administered to patients who suffer from inflammatory diseases, solid cancer (breast cancer, gastric cancer, large bowel cancer, colon cancer, rectal cancer, pancreatic cancer)

or lymphoma at a daily dosage of about 0.01 to 10 mg/kg. An adequate dosage is generally determined according to age, body weight, and conditions of a patient.

Hereinafter, the present invention will be described more specifically by the following working examples. However, the following working examples are provided only for illustrations and thus the present invention is not limited to or by them.

EXAMPLE 1

Synthesis of Polypeptides cDNA fragments of SEQ ID NOs: 18-22 encoding respective polypeptides of SEQ ID NOs: 9-13 were inserted into pET28a(+) vectors carrying cDNAs encoding the Fc regions of human immunoglobulin to produce five types of pET28a-hCD99-Fc vectors. That is, the cDNA fragments of SEQ ID NOs: 18-22 were isolated by PCR, digested with EcoRI, and inserted into the EcoRI sites of pET28a(+) vectors with ligation enzymes to produce the five types of the pET28a-hCD99-Fc vectors.

Colonies obtained by transforming BL21 (DE3) cells with the expression vectors, pET28a-hCD99-Fc, were cultured in LB media for about 4-6 hours. When the absorbance (A600) of the cultures reached 0.4-0.6, protein expression was induced by isopropyl β-D-1-thiogalactopyranoside (IPTG) (1.4 mM) for 7-9 hours. The cells were precipitated by centrifugation, washed with phosphate buffered saline (PBS), and precipitated to remove impurities from the media. Fractions were analyzed by SDS-PAGE gel to check protein expression.

For purification of expressed proteins, an 8M urea buffer (8M urea, 0.01M Tris-C1, 0.1M $NaH_2PO_4$) was used. The pH of the urea buffer was adjusted to 8.0, 6.3, 4.5, etc. according to a purification step. The cells were lysed with a pH 8.0 urea buffer containing protease inhibitors (1 mM PMSF, 10 □/□ leupeptin, 1 □/□, pepstatin, 1 □/□ aprotinin) and centrifuged at 13,000 rpm for 20 minutes at 4° C. The supernatants were mixed with histidine (His)-binding resins (Ni-NTA His Bind Resins, Novagen, U.S.A.) in a 1 □ Eppendorf tube, and the mixtures were incubated at 4° C. for 16 hours to induce the binding of histidine residues of the expressed proteins with the His-binding resins. The reaction solutions were centrifuged, the supernatants were discarded, and the pellets were washed with a pH 6.3 urea buffer. The protein was then eluted with a pH 4.5 urea buffer, dialyzed against PBS, and stored in aliquots in a cold store.

Polypeptides of SEQ ID NOs: 14-16 were synthesized with an automatic peptide synthesizer (PeptrEx-R48, Peptron, Daejeon, Korea) using a FMOC solid-phase method. The synthesized polypeptides were purified and analyzed by reverse-phase high-performance liquid chromatography (reverse-phase HPLC) (Prominence LC-20AB, Shimadzu, Japan) using a C18 analytical RP column (Shiseido capcell pak), and isolated using a mass spectrometer (HP 1100 Series LC/MSD, Hewlett-Packard, Roseville, U.S.A.). For optimization of EXPERIMENTAL EXAMPLEs 2, 3, 8, and 11 using mice as an experimental animal, a polypeptide derived from the mouse CD99 (SEQ ID No: 26) was also synthesized with the same methods in the above. The polypeptide of SEQ ID No: 26 corresponds to the polypeptide of SEQ ID No: 14 derived from human CD99.

The structures of polypeptides as set forth in SEQ ID NOs: 9-16 are illustrated in FIG. 1.

EXAMPLE 2

Preparation of Polypeptide-containing Compositions

The polypeptides of SEQ ID NOs: 9-13 were dissolved in PBS to a concentration of 3 □/100 □. Also, the polypeptides of SEQ ID NOs: 14-16 and 26 were dissolved in dimethylsulfoxide (DMSO) to a concentration of 3 □/□, and a saline solution was added thereto so that the concentration of each polypeptide was 20 □, 40 □, 80 □, or 100 □ based on the volume (100 □) of the final solution. The resultant protein solutions were used in the following experimental examples.

EXPERIMENTAL EXAMPLE 1

Tests for Inhibitory Activity of Polypeptides of the Present Invention Against Transmigration of Monocytes Human Umbilical Vein Endothelial Cells (HUVECs) were cultured in the upper compartments of Boyden chambers. The supernatants were removed, and human monocytes (U937), which had been untreated or treated with the compositions prepared in Example 2, were seeded at $5\times10^5$ cells/chamber. At this time, a culture including a chemo-attractant (a supernatant obtained by centrifugation of a culture obtained after culturing NIH/3T3 mouse fibroblasts in serum-free DMEM containing 0.005% vitamin C and 0.1% Bovine Serum Albumin (BSA) for 16 hours) was placed in the lower compartments of the chambers to induce the invasion of the monocytes. The chambers were incubated for 6 hours, and the number of the cells migrated to the lower compartments was measured. The test was repeated five times, and the results are illustrated in FIGS. 2 and 3. In FIG. 3, the "control peptide" is a peptide consisting of EEFD.

Referring to FIGS. 2 and 3, the number of migrated monocytes in the test groups treated with polypeptides according to the present invention was significantly reduced (about ⅔ reduction) as compared with that in the control group.

EXPERIMENTAL EXAMPLE 2

Tests for Inhibitory Activity of Polypeptides of the Present Invention Against Arthritis Effects of polypeptides of the present invention on rheumatoid arthritis (RA), one of representative inflammatory diseases, were tested. Type II collagen (10 mg/kg) was injected into mice (8-12 weeks old) to induce RA. A solution of a polypeptide of SEQ ID NO: 26 (40 or 80 □) in a saline solution (100 □) was intraperitoneally administered to the mice with RA at 2-day intervals (100 □ for each) for four weeks. As control groups, a saline solution (100 □) or a solution of methotrexate (MTX, 100 □) used as an anti-inflammatory agent in a saline solution (100 □) was intraperitoneally administered to the mice with RA.

The onset and severity of arthritis in each experimental group were visually determined, and the arthritis index was measured using a method known in the art (SI Lee, P M Hyun, S H Kim, K S Kim, S K Lee, B S Kim, P J Maeng, and J-S Lim (2005) Suppression of the Onset and Progression of Collagen-Induced Arthritis by Chebulagic Acid Screened From a Natural Product Library. Arthritis Rheum 52: 345). The results are illustrated in FIG. 4. In FIG. 4, CIA represents collagen-induced arthritis. Referring to FIG. 4, in the test groups treated with the polypeptide of the present invention, arthritis indices began to decrease 2 weeks after the polypeptide treatment. At 4 weeks after the polypeptide treatment, the arthritis indices were reduced to about ⅓ of those of the control groups.

Meanwhile, the degree of corrosion of articular cartilages of normal mice with no RA and the above CIA mice was measured. That is, the knee joint tissues of the hind legs of the normal mice with no RA, saline-treated CIA mice, MTX-treated CIA mice, and CIA mice treated with a solution of a polypeptide of SEQ ID NO: 26 (80 □) in a saline solution (100 □) were harvested. The harvested tissues were fixed in 10% formalin, decalcified with 5% formic acid, processed into paraffin blocks, cut into 5 □ sections, and stained with haematoxylin and eosin or Masson's trichrome, and examined with a microscope (at 200× magnification). The results are shown in FIG. 5.

Referring to FIG. 5, severe corrosion and invasion of leukocytes were observed in the articular cartilages of the CIA mice, as compared with the normal mice. In contrast, corrosion of articular cartilages and invasion of leukocytes in the CIA mice treated with the polypeptide of SEQ ID NO: 26 according to the present invention were diminished to the extent that was observed in the normal mice and the MTX-treated CIA mice.

EXPERIMENTAL EXAMPLE 3

Tests for Inhibitory Activity of Polypeptides of the Present Invention Against Transmigration of Lymphocytes and Myeloid Cells in the Spleens A polypeptide of SEQ ID NO: 26 (40 MOOD) was intraperitoneally administered to mice with RA, which had been induced in the same manner in EXPERIMENTAL EXAMPLE 2, at 2-day intervals for 4 weeks. Normal mice, saline-treated RA mice with intraperitoneal injection of a saline solution, and MTX-treated RA mice with intraperitoneal injection of a solution of MTX (100 □) in a saline solution (100 □) were used as control groups. Spleen tissues were harvested from the mice of all the experimental groups and washed with RPMI 1640 media, and single cells were isolated. After the total number of the single cells were counted, the single cells were stained with monoclonal antibodies (anti-$CD3^+$, $CD4^+$, $CD8^+$, $CD11^+$, $CD19^+$, $CD69^+$, $Gr-1^+$) capable of labeling T cells ($CD3^+$, $CD4^+$, $CD8^+$), activated T cells ($CD3^+$, $CD69^+$), B cells ($CD19^+$), and myeloid cells ($CD11^+$, $Gr-1^+$), and flow cytometry analysis was performed. The number of lymphocytes and myeloid cells migrated to joint spaces was measured by determining the number of the T cells, the activated T cells, the B cells, and the myeloid cells per total cell number, and the results are illustrated in FIG. 6.

Referring to FIG. 6, the migrated cell numbers for the T cells ($CD3^+$, $CD4^+$, $CD8^+$), the activated T cells ($CD3^+$, $CD69^+$), the B cells ($CD19^+$), and the myeloid cells ($CD11b^+$, $Gr-1^+$) in the test group treated with the polypeptide according to the present invention were similar to those of the MTX-treated group, and were reduced to about ⅔ of those of the saline-treated group.

EXPERIMENTAL EXAMPLE 4

Tests for Inhibitory Activity of Polypeptides of the Present Invention Against Migration of T Cells (Cd3+), B Cells (Cd19+), and Myeloid Cells (Cd11B+, Gr-1+) into the Joint Spaces As well known, when inflammation develops in joints, lymphocytes and myeloid cells of different differentiation stages invade joint spaces. Thus, effects of polypeptides according to the present invention on invasion of lymphocytes and myeloid cells into joint spaces were tested.

The polypeptide of the present invention, a saline solution, or MTX was administered to RA mice in the same manner as in EXPERIMENTAL EXAMPLE 3, and synovial fluid was obtained from the joint spaces of the mice of all the experimental groups. After the total cell number in the synovial fluid was counted, flow cytometry analysis was performed in the same manner as in EXPERIMENTAL EXAMPLE 3 to measure the number of T cells ($CD3^+$), B cells ($CD19^+$), and myeloid cells ($CD11b^+$, $Gr-1^+$) migrated to the joint spaces. The results are illustrated in FIG. 7.

Referring to FIG. 7, the number of T cells ($CD3^+$, $CD4^+$, $CD8^+$), B cells ($CD19^+$), and myeloid cells ($CD11b^+$, $Gr-1^+$) migrated to joint spaces in the polypeptide-treated group according to the present invention was similar to that of the MTX-treated group and was reduced to about 50-70% of that of the saline-treated group.

EXPERIMENTAL EXAMPLE 5

Tests for Inhibitory Activity of Polypeptides of the Present Invention Against Expression of TNF-α and INF-γ

When inflammation occurs, invasion of T cells into peripheral lymph nodes increases, and the expression levels of TNF-α and INF-γ which are secreted from the T cells also increase. Thus, effects of polypeptides according to the present invention on the expression of TNF-α and INF-γ were tested.

RA was induced in mice in the same manner as EXPERIMENTAL EXAMPLE 2, and a saline solution, MTX, or a polypeptide according to the present invention was administered to the RA mice. Then, sera were isolated from all the experimental groups, and the expression levels of TNF-α and INF-γ were measured using ELISA. The results are illustrated in FIGS. 8 and 9.

Referring to FIGS. 8 and 9, the expression levels of TNF-α and INF-γ in the polypeptide-treated group according to the present invention were similar to those of the MTX-treated group and were reduced to about 50% of those of the saline-treated group.

EXPERIMENTAL EXAMPLE 6

Tests for Inhibitory Activity of Polypeptides of the Present Invention Against Adhesion of HUVEC to Extracellular Matrix Effects of polypeptides of SEQ ID NOs: 9-16 on adhesion of HUVEC to fibronectin were tested.

Each well of a 96-well culture plate was coated with fibronectin, a component of extracellular matrix, for 6 hours under UV light, and then blocked with 1% heat-inactivated BSA for 1 hour. HUVEC cells ($5 \times 10^4$) were dispensed into each well, and then the protein solution prepared in Example 2 was added to the well. After incubation in 5% $CO_2$ at 37° C. for 1 hour, the cells were gently washed three times with PBS, and then detached using trypsin-EDTA and stained with a trypan-blue solution. The number of the cells was determined using a hemacytometer. The results are illustrated in FIGS. 10 and 11.

Referring to FIGS. 10 and 11, in the test groups treated with the polypeptides of the present invention, the number of HUVECs adhered to fibronectin was reduced by about 10-40% relative to a control group. However, in the test group treated with the polypeptide of SEQ ID NO: 12 including no amino acids at positions 94-97 of SEQ ID NO: 1, the degree of adhesion of HUVECs to fibronectin was similar to that of the control group. Thus, it is anticipated that polypeptides of the present invention including peptides at positions 94-97 of SEQ ID NO: 1 can inhibit angiogenesis.

EXPERIMENTAL EXAMPLE 7

Tests for Inhibitory Activity of Polypeptides of the Present Invention Against in vitro Tube Formation Interactions of basement membrane components of blood vessels with vascular endothelial cells play an important role in formation and maintenance of new blood vessels. Thus, effects of polypeptides of the present invention on tube formation were evaluated.

HUVECs were plated at a density of $8 \times 10^4$ cells/well to each well of 24-well culture plates coated with Matrigel. The protein solution including the polypeptide of SEQ ID NO: 9 (30 □/□) prepared in Example 2, secondary antibody (Goat anti-mouse IgG; Dinona, Korea), or a mixture thereof was added to the wells, and the cells were cultured in media 199 containing 20% fetal bovine serum (FBS), penicillin (100 units/□), streptomycin (100 □/□), bFGF (3 ng/□), and heparin (5 units/□) in a CO2 incubator maintained at 5% $CO_2$ partial pressure and a temperature of 37° C. for 24 hours. Formation of new blood vessels was examined using an inverted microscope (at 50× magnification), and the results are shown in FIG. 12.

Referring to FIG. 12, when HUVECs were treated with the protein solution including the polypeptide of the present invention, tube formation was significantly reduced.

EXPERIMENTAL EXAMPLE 8

Tests for Inhibitory Activity of Polypeptides of the Present Invention Against in vivo Tumor Development and Angiogenesis B16-F10-Luc-G5 (mouse melanoma cell line, Xenogen, U.S.A.) was injected into the subcutaneous fat tissues of the backs of 10 male nude mice (5 weeks old) ($1.5 \times 10^5$ cells/mouse). At 48 hours after the injection, the mice were divided into five mice for a test group and five mice for a control group. In the test group, a polypeptide (100 □) of SEQ ID NO: 26 was intraperitoneally administered to each mouse at a 48-hour intervals. Tumor cells were injected into the test group and the control group, and from 12 days after the injection of the tumor cells, a tumor volume was measured. The tumor volume was calculated by the formula: $(L \times W)^2 \times H \times 0.5$ where L, W, and H are respectively the length, width, and height of tumor.

At 14 days after the injection of the tumor cells, tumor tissues were excised from the mice, fixed in 4% paraformaldehyde, washed with water, processed into paraffin blocks, cut into 5 □ standard frontal sections, and stained with haematoxylin and eosin, and examined with a microscope (at 40× magnification) to compare the degree of angiogenesis.

FIG. 13 is images showing the degree of development of melanoma (A) and the degree of angiogenesis (B) in the control group and the test group treated with the polypeptide of the present invention. Referring to FIG. 13, in the test group treated with the polypeptide of the present invention, the development of melanoma and angiogenesis were significantly reduced as compared with those of the control group.

FIG. 14 is a graph illustrating melanoma tumor volumes in the control group and the test group treated with the polypeptide of the present invention. Referring to FIG. 14, in the test group treated with the polypeptide of the present invention, melanoma volume at 12 days after the injection of the tumor cells was reduced to about ⅙ of that of the control group.

EXPERIMENTAL EXAMPLE 9

Tests for Inhibitory Activity of Polypeptides of the Present Invention Against in vitro Transmigration of Cancer Cells Transendothelial migration assays for MCF-7 human breast carcinoma cells were performed in polycarbonate transwell inserts (8-□ pore; Costar, Corning, N.Y.) coated with HUVECs and grown as a monolayer for 24 hours. MCF-7 cells were resuspended in serum-free RPMI-1640 and were preincubated with 10 □ of a control peptide consisting of EEFD or 10 □ of a peptide of SEQ ID NO: 16 for 1 hour before plating. HUVEC cells were also treated as described above at the same time. Typically, $5 \times 10^5$ MCF-7 cells were seeded in the upper compartment, and chemo-attractant (described in EXPERIMENTAL EXAMPLE 1) was placed in the lower compartment. After 6 hours at 37° C., the number of MCF-7 cells that had migrated through the monolayer was determined by direct counting.

FIG. 15 is a graph illustrating the number of transmigrated cells in the experiment described above. Referring to FIG. 15, the number of transmigrated MCF-7 cells in the test groups was reduced to about 60% of that in the control group. Taking into consideration that transmigration is essential for migration of cancer cells into organs through blood vessels, it is anticipated that polypeptides of the present invention can effectively inhibit the migration of cancer cells.

EXPERIMENTAL EXAMPLE 10

Tests for Inhibitory Activity of Polypeptides of the Present Invention Against Invasion of Cancer Cells Cell migration was measured using a Transwell migration apparatus(Costar, Inc., Cambridge, United Kingdom). The filters (8-□ pore size) were coated with 1 mg/ml fibronectin-solution on top surface. MCF-7 cells were treated with a polypeptide of SEQ ID NO: 14 (10 □, 50 □, 100 □), incubated in a 5% CO2 incubator at 37° C. for 1 hour, and then washed with serum-free RPMI-1640. MCF-7 cells ($2.4 \times 10^5$ cells) were loaded to the upper chamber of the Transwell, whereas chemo-attractant described above were loaded into the lower chamber. Cells migrated into the lower chambers of the Transwell were counted three times at 24-hour intervals, and then the results were stastically analyzed.

FIG. 16 is a graph illustrating the number of the human breast cancer cells that have invaded fibronectin after administration of the polypeptide of the present invention. Referring to FIG. 16, in the test groups treated with the polypeptide of the present invention, the invasion rate of the human breast cancer cells was reduced by about 50% relative to that of a control group treated with a peptide consisting of EEFD-DAEEFDD (SEQ ID NO: 27). Taking into consideration that cancer cells from blood vessels invade basement membranes or surrounding connective tissues and then spread to secondary sites, it is anticipated that polypeptides of the present invention can effectively inhibit the metastasis of cancer cells.

EXPERIMENTAL EXAMPLE 11

Tests for Inhibitory Activity of Polypeptides of the Present Invention Against in vivo Transmigration of Cancer Cells B16-F10-Luc-G5 cells (mouse melanoma cell line, Xenogen, U.S.A.) were injected into the tail veins of 10 nude mice (5 weeks old). The nude mice were divided into five mice for a control group and five mice for a test group. The control group was injected with a mixture of PBS with a peptide consisting of EEFDDAEEFDD (SEQ ID NO: 27) (control peptide) and the test group with a mixture of PBS with 100 μg of a peptide of SEQ ID NO: 26. The control peptide and the peptide of SEQ ID NO: 26 were intraperitoneally administered to the control group and the test group, respectively, at 2-day intervals for 15 days. Then, the nude mice were dissected and the lungs and livers were excised from the nude mice. Tumor nodules were counted.

FIG. 17 is images (A) showing melanoma nodules that have spread to the lungs and livers of the mice of the control group and the test group through transmigration and a comparative graph (B) illustrating the number of the melanoma nodules. Referring to FIG. 17, the degree of spread of melanoma in the test group treated with the polypeptide of the present invention was reduced to about 40% of that of the control group.

Industrial Applicability

A polypeptide or its fusion protein according to the present invention can inhibit the transmigration of leukocytes or the growth and/or metastasis of cancer cells.

The invention claimed is:

1. A contiguous polypeptide fragment consisting of 4 to 130 amino acids of SEQ ID NO: 1, said polypeptide comprising the amino acid sequence from position 94 to position 97 of SEQ ID NO: 1.

2. The polypeptide fragment of claim 1, which is one selected from the group consisting of the polypeptides as set forth in SEQ ID NOs: 2-8.

3. The polypeptide fragment of claim 1, which is one selected from the group consisting of polypeptides as set forth in SEQ ID NOs: 9-11 and 13-16.

4. A fusion protein wherein a polyhistidine (poly-His) region is fused to the polypeptide fragment of claim 1.

5. The fusion protein of claim 4, wherein the poly-His region has an amino acid sequence as set forth in SEQ ID NO: 17.

6. A pharmaceutical composition for inhibiting transmigration of leukocytes, comprising the polypeptide fragment of claim 1 as an active ingredient and a pharmaceutically acceptable carrier.

7. A pharmaceutical composition for inhibiting transmigration of leukocytes, comprising, as an active ingredient a fusion protein wherein a poly-His region is fused to the polypeptide fragment of claim 1, and a pharmaceutically acceptable carrier.

8. A pharmaceutical composition for inhibiting the growth and/or metastasis of cancer cells, wherein the cancer cell is selected from the group consisting of breast cancer cells, gastric cancer cells, large bowel cancer cells, colon cancer cells, rectal cancer cells, pancreatic cancer cells, melanoma cells and lymphoma, comprising the polypeptide fragment of claim 1 as an active ingredient and a pharmaceutically acceptable carrier.

9. A pharmaceutical composition for inhibiting the growth and/or metastasis of cancer cells, wherein the cancer cell is selected from the group consisting of breast cancer cells, gastric cancer cells, large bowel cancer cells, colon cancer cells, rectal cancer cells, pancreatic cancer cells, melanoma cells and lymphoma, comprising, as an active ingredient, a fusion protein in which a poly-His region is fused to the polypeptide fragment of claim 1, and a pharmaceutically acceptable carrier.

10. A method for inhibiting transmigration of leukocytes, comprising administering the pharmaceutical composition of claim 6 to a subject in need.

11. A method for inhibiting transmigration of leukocytes, comprising administering the pharmaceutical composition of claim 7 to a subject in need.

12. A method for inhibiting the growth and/or metastasis of cancer cells, wherein the cancer cell is selected from the group consisting of breast cancer cells, gastric cancer cells, large bowel cancer cells, colon cancer cells, rectal cancer cells, pancreatic cancer cells, melanoma cells and lymphoma, comprising administering the pharmaceutical composition of claim 8 to a subject in need.

13. A method for inhibiting the growth and/or metastasis of cancer cells, wherein the cancer cell is selected from the group consisting of breast cancer cells, gastric cancer cells, large bowel cancer cells, colon cancer cells, rectal cancer cells, pancreatic cancer cells, melanoma cells and lymphoma, comprising administering the pharmaceutical composition of claim 9 to a subject in need.

\* \* \* \* \*